United States Patent
Weiss et al.

(10) Patent No.: US 9,062,353 B2
(45) Date of Patent: *Jun. 23, 2015

(54) ELECTRICALLY CONDUCTIVE POLYMER ELECTRODES WITH INCORPORATED VIRUSES

(71) Applicant: THE REGENTS OF THE UNIVERSITY OF CALIFORNIA, Oakland, CA (US)

(72) Inventors: Gregory A. Weiss, Irvine, CA (US); Reginald M. Penner, Newport Beach, CA (US); Jessica A. Arter, Laguna Beach, CA (US); David K. Taggart, Mission Viejo, CA (US); Keith C. Donavan, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/960,703

(22) Filed: Aug. 6, 2013

(65) Prior Publication Data

US 2014/0030699 A1 Jan. 30, 2014

Related U.S. Application Data

(62) Division of application No. 13/251,923, filed on Oct. 3, 2011, now Pat. No. 8,525,237.

(60) Provisional application No. 61/389,434, filed on Oct. 4, 2010.

(51) Int. Cl.
*C12Q 1/70* (2006.01)
*G01N 27/12* (2006.01)
*C12Q 1/68* (2006.01)

(52) U.S. Cl.
CPC ............... *C12Q 1/70* (2013.01); *G01N 27/127* (2013.01); *C12Q 1/6825* (2013.01); *C12Q 1/701* (2013.01)

(58) Field of Classification Search
CPC . G01N 27/127; G01N 27/007; C12Q 1/6825; C12Q 1/701; C12Q 1/70; C12Q 2563/116; C12Q 2563/137; C12Q 2563/157
See application file for complete search history.

(56) References Cited

U.S. PATENT DOCUMENTS

| | | | |
|---|---|---|---|
| 5,571,698 A | 11/1996 | Ladner et al. | |
| 8,525,237 B1 * | 9/2013 | Weiss et al. ................... | 257/253 |
| 2006/0148100 A1 | 7/2006 | Madison et al. | |
| 2008/0097280 A1 | 4/2008 | Martin et al. | |
| 2009/0092965 A1 | 4/2009 | Weiss et al. | |
| 2009/0197209 A1 | 8/2009 | Penner et al. | |

FOREIGN PATENT DOCUMENTS

| | | |
|---|---|---|
| WO | WO 88/06630 | 9/1988 |
| WO | WO 92/01047 | 1/1992 |

OTHER PUBLICATIONS

Gern et al. (2007) "Inhibition of Rhinovirus Replication In Vitro and In Vivo by Acid-Buffered Saline", The Journal of Infectious Diseases, 195(8): 1137-43.*
PCT International Search Report for PCT/US2011/054736, Applicant: The Regents of the University of California, Form PCT/ISA/210 and 220, Docket No. 2010-772-2WO, dated May 2, 2012 (9 pages).
PCT Written Opinion of the International Search Authority for PCT/US2011/054736, Applicant: The Regents of the University of California, Form PCT/ISA/237, Docket No. 2010-772-2WO, dated May 2, 2012 (5pages).
Asplund, Maria et al., Composite biomolecule/PEDOT materials for neural electrodes, Biointerphases 2008, 3, 83-93.
Arter, Jessica A. et al., Virus-PEDOT Nanowires for Biosensing, Nano Lett. 2010, 10, 4858-4862.
Baek, Hyunjung et al., An Improved helper phage system for efficient isolation of specific antibody molecules in phage display, Nucleic. Acids Res. 30, No. 5 e18, 2002.
Boder, Eric T. et al., Yeast surface display for screening combinatorial polypeptide libraries, Nat. Biotechnol. 15:553-7, 1997.
Donovan, William et al., Genes Encoding Spore Coat Polypeptides from *Bacillus subtilis*, J. Mol. Biol. 196: 1-10, 1987.
Georgiou, George et al., Display of heterologous proteins on the surface of microorganisms: From the screening of combinatorial libraries to live recombinant vaccines, Nat. Biotechnol. 15: 29-34, 1997.
Griffiths, Andrew D. et al., Human anti-self antibodies with high specificity from phage display libraries, EMBO J. 12: 725-34, 1993.
Han, Xiaoliang et al., Ligand-directed retroviral targeting of human breast cancer cells, Proc. Natl. Acad. Sci. USA 92: 9747-9751, 1995.
Kunkel, Thomas A. et al., Rapid and Efficient Site-Specific Mutagenesis without Phenotypic Selection, Methods Enzymol. 1987, 154, 367-382.
Levin, Aron M. et al., Double Barrel Shotgun Scanning of the Caveolin-1 Scaffolding Domain, ACS Chem. Biol. 2007, 2, 493-500.
Marzari, Roberto et al., Phage display of *Bacillus thuringiensis* CrylA(a) insecticidal toxin, FEBS Lett. 411: 27-31, 1997.

(Continued)

*Primary Examiner* — Robert M Kelly
(74) *Attorney, Agent, or Firm* — Vista IP Law Group LLP

(57) ABSTRACT

Grafting M13 bacteriophage into an array of poly(3,4-ethylenedioxythiophene) (PEDOT) nanowires generated hybrids of conducting polymers and replicable genetic packages (rgps) such as viruses. The incorporation of rgps into the polymeric backbone of PEDOT occurs during electropolymerization via lithographically patterned nanowire electrodeposition (LPNE). The resultant arrays of rgps-PEDOT nanowires enable real-time, reagent-free electrochemical biosensing of analytes in physiologically relevant buffers.

19 Claims, 12 Drawing Sheets

(56) References Cited

OTHER PUBLICATIONS

Murase, Katsuyuki et al., EF-Tu Binding Peptides Identified, Dissected, and Affinity Optimized by Phage Display, Chem. Biol. 2003, 10, 161-168.

Sblattero, Daniele et al., In vivo recombination as a tool to generate molecular diversity in phage antibody libraries, Rev. Mol. Biotechnol. 74: 303-15, 2001.

Sidhu, Sachdev et al., Phage Display for Selection of Novel Binding Peptides, Methods Enzymol. 2000, 328, 333-363.

Xiao, Y.H. et al., Adenosine 5'-triphosphate incorporated poly(3,4-ethylenedioxythiophene) modified electrode: a bioactive platform with electroactivity, stability and biocompatibility, J. Appl. Electrochem. 2008, 38, 1735-1741.

Yang, Li-Mei C. et al., Virus Electrodes for Universal Biodetection, Anal. Chem. 2006, 78, 3265-3270.

Oliphant, Arnold R. et al., Cloning of random-sequence oligodeoxynucleotides, Gene 44: 177-183, 1986.

* cited by examiner

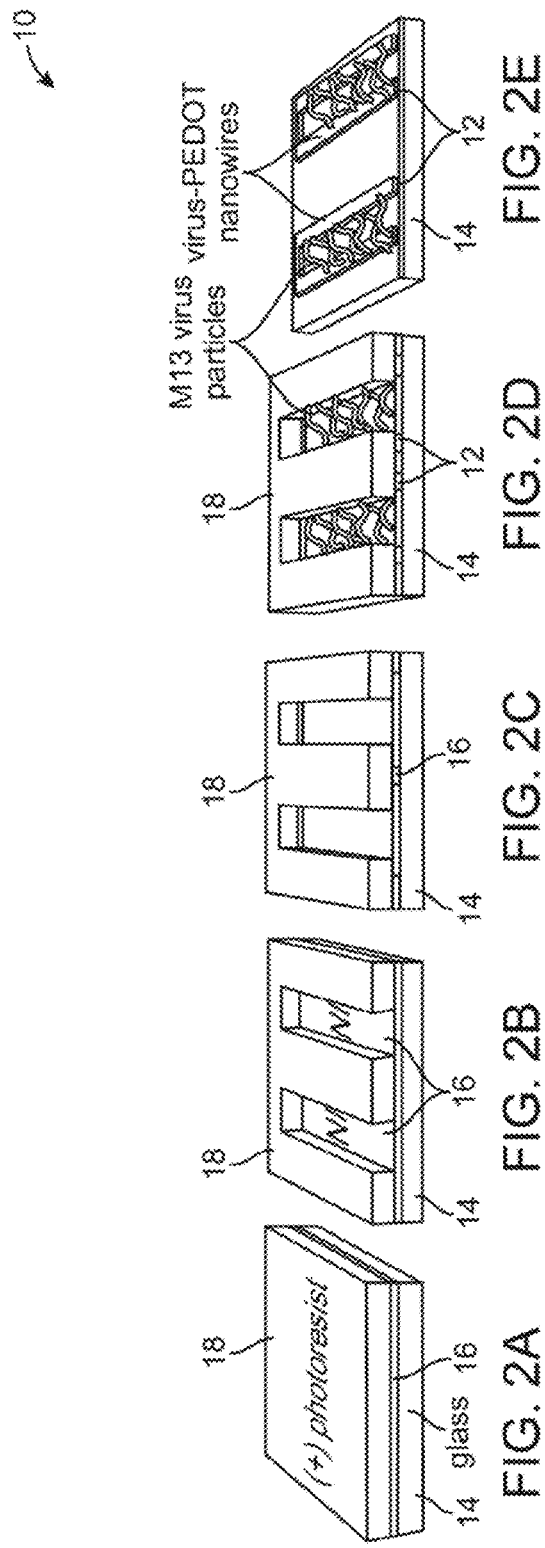

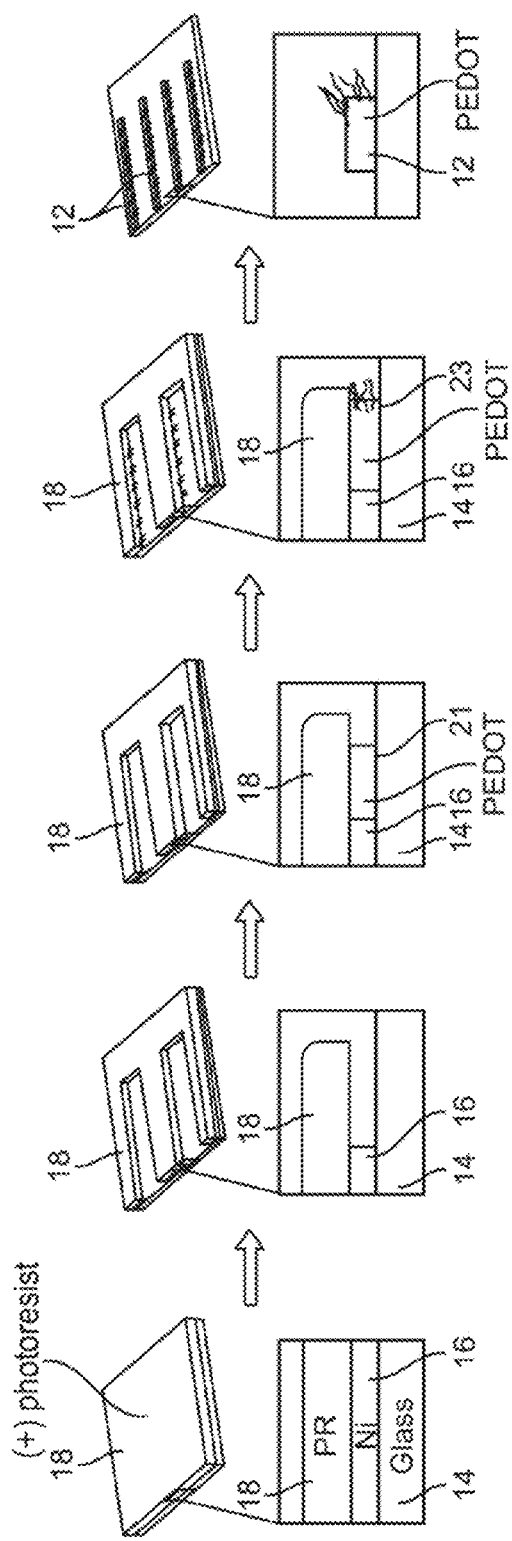

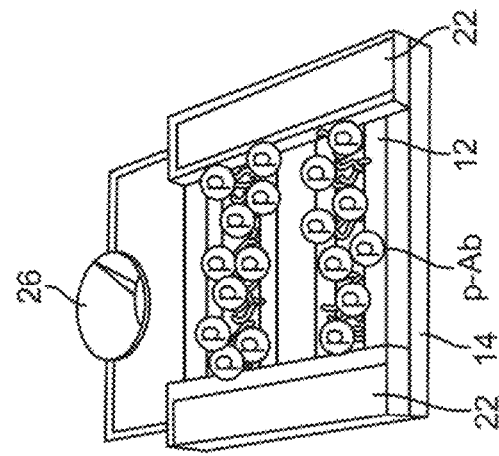
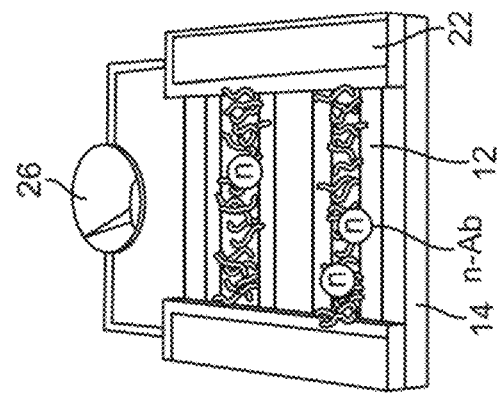
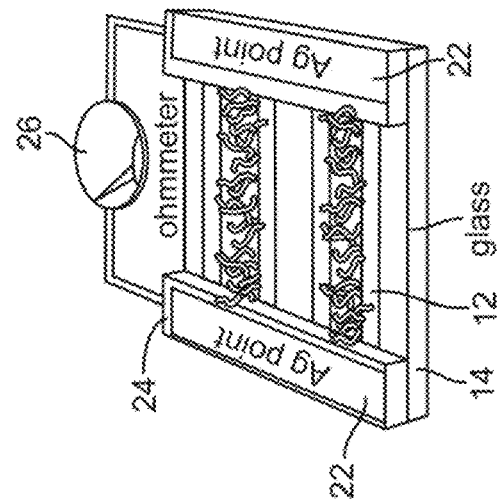

ELECTRICALLY CONDUCTIVE POLYMER ELECTRODES WITH INCORPORATED VIRUSES

RELATED APPLICATION

This application is a divisional of U.S. patent application Ser. No. 13/251,923 filed on Oct. 3, 2011, now issued as U.S. Pat. No. 8,525,237, which claims priority to U.S. Provisional Patent Application No. 61/389,434 filed on Oct. 4, 2010. Priority is claimed pursuant to 35 U.S.C. §119 and 120. The above-noted patent applications are incorporated by reference as if set forth fully herein.

STATEMENT REGARDING FEDERALLY SPONSORED RESEARCH OR DEVELOPMENT

This invention was made with Government support under Grant Nos. AI074163, CA119551, and CA133592 awarded by the National Institutes of Health, and Grant No. CHE0956524 awarded by the National Science Foundation. The Government has certain rights in this invention.

FIELD OF THE INVENTION

The field of the invention generally relates to biosensors and other electronic devices requiring viruses directly incorporated into electronic circuits. More particularly, the field of the invention generally relates to reagent-free detection of biomarkers using viruses incorporated into an electrically conductive nanowire.

BACKGROUND

Biosensors are analytical devices that allow for the detection of one or more analytes or species using a biological constituent for molecular recognition in combination with a detector component. The detection aspect of biosensors may operate based on the transduction of, optical or electrochemical changes that occur in response to the presence or binding of the analyte or species with the biological constituent. Many biosensors require that a label be attached to a target analyte. The amount or some proxy of the amount of label is detected and assumed to correspond to the number of target molecules. Labels can include fluorophores, magnetic beads, enzymes that generate a detectable species, or the like. Labels, however, can be expensive and can increase the overall time of the detection process. Some approaches, such as electrical-based biosensors, have attempted to eliminate the use of labels. A variety of different electrical measurements can be used in electrical-based biosensors. For instance, there are voltammetric sensors, amperometric/coulometric sensors, and impedance sensors.

Phage-displayed peptide libraries have been investigated as a potential tool that could offer the ability to test or screen for a large number of target molecules. For example, phage-displayed peptide libraries having on the order of $10^{10}$ unique members offer the promise of universal biorecognition. Unfortunately, this technology has found only limited application in biosensors. In prior work, detecting molecular recognition between phage and target has focused on a "sandwich assay" scheme involving the detection of phage binding to immobilized target using rather complicated and expensive testing equipment.

In some instances, the molecular recognition elements are covalently bound or otherwise linked to the electrode surface. For example, U.S. Patent Application Publication No. 2009-0092965 describes a biosensor device that uses a self-assembled monolayer that is interposed between an electrode and the bound virus particles. Sometimes, however, the linking chemistry is not always reliable and the required surface functionalization processes can be time consuming.

Nanowires offer versatile and unique properties for use in chemical and biological sensing applications. The chemical sensitivity of nanowires typically results from their high surface-to-volume ratios. The nanometer-scale, in addition to providing capacity for high-density parallelization, is well suited for biological systems. Interest in nanowire-based sensors derives primarily from the potential for such sensors to be label- and reagent-free; direct electrical sensing with nanowires could ultimately deliver a real-time device with the attributes of small size, low cost, and potential for high-throughput measurements.

Conventional nanowire biosensors use semiconducting nanowires, surface-modified with receptors such as antibodies, in a field-effect transistor configuration. The binding of a charged analyte molecule to these receptors induces a conductivity change in the nanowire by coulombically accumulating or depleting charge carriers. Silicon and indium oxide semiconductor nanowires, for example, have been used to directly sense pH, metal ions, small molecules, proteins, lipoproteins, and DNA. Nanowires have also been used as the basis for biosensors that detect virus particles.

Conducting polymers, such as polythiophene, polypyrrole, and PEDOT, provide new opportunities for the incorporation of receptors into nanowires for biosensing. In contrast to metals and inorganic semiconductors, conducting polymers have a high degree of structural malleability and flexibility; additionally, conducting polymers offer some degree of porosity to potentially allow access to solvent and prospective analyte molecules. Nanoparticles, nanowires, and other sub-micron scale structures have been synthesized to allow tunable charge-transport, and offer a wide range of chemical and physical properties. For measurements in biological systems, the stability to physiological conditions of conducting polymer nanowires provides high intrinsic biocompatibility. Doped conducting polymers have inherent electrical conductivity resulting from the presence of charge carriers and the mobility of the carriers in a conjugated system. Conducting polymer-based sensors have been used to detect ammonia, chloroform, hydrogen, acetic acid, and other compounds.

The specificity and selectivity of conducting polymer biosensors, either in thin films or nanowires, can be customized with biomolecules providing molecular recognition. The syntheses of conducting polymers can be made compatible with the integration of biomolecules, which typically require aqueous conditions at moderate temperatures and neutral pH. Approaches to incorporate biomolecules into conducting polymers include attachment to a monomer before polymerization, entrapment during synthesis, or conjugation after synthesis. To date, immobilized recognition elements include metal ions, antibodies, DNA, proteins, and enzymes. Viruses, which offer versatile platforms for molecular recognition, have not been previously incorporated into conducting polymer nanowire-based biosensors.

M13, a bacteria infecting virus or bacteriophage, can recognize essentially any analyte by binding to engineered polypeptides displayed on its surface, which can be altered through manipulation of the phage-packaged DNA. The protein coat of the virus provides densely packed receptors for avidity-based binding to analytes. Thus, the receptors selected from phage-displayed libraries can bind to small molecules, proteins, DNA, and viruses. Inexpensive, readily produced, and available in large quantities, these viruses infect only their host *E. coli* bacteria. M13 viruses can also form films patterned by an underlying polymer, or template the synthesis of materials through binding to phage-displayed peptides. With proven capabilities for engineered molecular recognition and materials, viruses could provide new approaches to electrical conductivity-based biosensing.

Even if nanowires are desirable from a biosensor perspective, several technical hurdles need to be surmounted. For example, arbitrary patterns of conductive polymer nanowires need to be fabricated in a controlled yet high-throughput manner. Further, custom molecular recognition motifs need to be integrated into the nanowires. Further, the molecular recognition scaffolds need to tolerate the harsh conditions of fabrication.

SUMMARY

The obstacles referred to in the Background have been solved by the techniques and methods described herein. M13 phage viruses have successfully been incorporated into nanowire arrays. The resultant label-free biosensing platform allows direct electrical resistance measurements to detect low concentrations of target analytes. Target analytes include clinically relevant biomarkers such as, for example, prostate-specific membrane antigen (PSMA), a protein that is associated with prostate cancer diagnosis. It is one object of the present invention to provide methods and compositions for the incorporation of replicable genetic packages (rgps) into biosensors.

In one embodiment, a biosensor is formed by polymer-based nanowires having rgps (e.g., viruses) incorporated therein. The polymer-based nanowire can include, for example, poly(3,4-ethylenedioxythiophenes) (PEDOT) nanowire having phage virus particles incorporated therein. Using lithographically patterned nanowire electrodeposition, PEDOT nanowires are electropolymerized at the surface of an electrode. In exemplary embodiments described hereinafter, inclusion of bacteriophage (e.g., M13) in the growth solution allows for incorporation of the phage into the PEDOT polymer. After etching, the isolated PEDOT nanowires (or films) with phage incorporated therein remain. Bacteriophage bear an overall net negative charge at their surface, while still displaying peptides or proteins of interest on their coats. Electrical resistance measurements can then be used for real-time detection of analytes. Importantly, there is no need for any labels as the target analyte can be detected directly through the interaction with the phage that is integrated into the nanowires. A biosensor incorporating a nanowire offers both real-time and label-free functionality. Various recognition ligands can be attached to the phage coat protein, and upon incorporation of the phage into the PEDOT nanowire (or film), changes in electrical resistance can indicate binding to analytes. Alternatively, the phage can display redox active enzymes driven by direct electrical current.

In another embodiment of the invention, a method of making an electrically conductive polymer nanowire is disclosed. The method involves depositing a metallic film on a substrate; coating the metallic film with a photoresist; patterning the photoresist to define desired portions of nanowires; removing portions of the exposed metallic film through oxidative degradation; wherein said removal includes the formation of a side-exposed trenches underlying portions of the photoresist; electrodepositing PEDOT nanowires in the side-exposed trenches (which may contain viruses); removal of the photoresist; and etching the remains of the metallic film. These PEDOT nanowires are then free-standing isolates on a glass substrate.

In yet another embodiment of the invention, a biosensor includes a substrate containing a plurality of virus (or other rgps)-PEDOT nanowires and a resistance measuring device operatively coupled to the plurality of rgps-PEDOT nanowires.

BRIEF DESCRIPTION OF THE DRAWINGS

FIGS. 2A-2E illustrate a schematic representation of the lithographically patterned nanowire electrodeposition (LPNE) process.

FIG. 3A-3E illustrate another schematic representation of the lithographically patterned nanowire electrodeposition (LPNE) process. Cross-sectional views of the substrate, metal layer, photoresist, and PEDOT nanowire are illustrated.

FIGS. 4A-4C illustrates a schematic of a biosensor device with a resistance measuring device coupled to the biosensor. FIG. 4A illustrates the biosensor device with no sample. FIG. 4B illustrates the biosensor device exposed to a negative control antibody (n-Ab). FIG. 4C illustrates the biosensor device exposed to a positive antibody (p-Ab), capable of binding to M13 viruses.

DETAILED DESCRIPTION OF THE ILLUSTRATED EMBODIMENTS

The method and device described herein solves the concerns raised above in the Background section. While described in detail hereinafter with respect to filamentous phage M13, in various embodiments the rgps that find use in these methods may be any that are commonly used in the art for polypeptide display methods, including bacteriophage (e.g., lambda, T-even phage such as T4, T-odd phage such as T7, etc.), spores, bacteria, yeast, eukaryotic viruses, etc. Moreover, phagemid/helper phage and other "two vector" phage packaging systems are also within the scope of the present invention. See e.g., Baek et al., Nucleic. Acids Res. 30, No. 5 e18, 2002; Sblattero et al., Rev. Mol. Biotechnol. 74: 303-15, 2001; Marzari et al., FEBS Lett. 411: 27-31, 1997, which is incorporated by reference herein.

In preferred embodiments, the rgps are bacteriophage, more preferably filamentous phage, and most preferably M13, fd, fl, or engineered variants thereof. Thus, in particularly preferred embodiments, the present invention relates to using these as platforms for phage display of target molecules on a biosensor. The rgps component of the device displays a heterologous molecule on its surface. The heterologous molecule may include peptides, nucleic acids, antibody binding domains, receptor ligands, and the like.

Figure 1A:
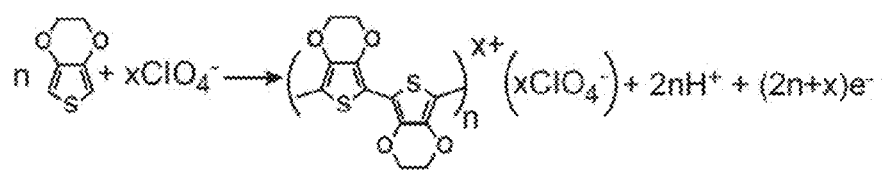
FIG. 1A illustrates the polymerization reaction of EDOT
Figure 1B:
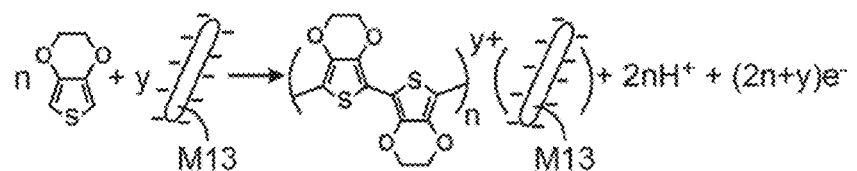
FIG. 1B illustrates the polymerization reaction of EDOT with virus (M13) incorporation.

Difficulties incorporating viruses into metal nanowires necessitated development of a new lithographically patterned nanowire electrodeposition (LPNE) synthesis using the water-soluble EDOT monomer. FIG. 1A illustrates the polymerization reaction of EDOT. FIG. 1B illustrates the polymerization reaction of EDOT with virus (M13) incorporation. This approach offers chemical and biological selectivity to the nanowire arrays, without requiring post-synthesis functionalization. The resultant label-free biosensing platform allows direct electrical resistance measurements to detect low concentrations of target analytes.

The LPNE method was used to create devices 10 with linear arrays of several hundred virus-PEDOT hybrid nanowires 12 on a substrate 14. This process is illustrated in FIGS. 2A-2E, and FIGS. 3A-3E. As best seen in FIGS. 2A and 3A, a substrate 14 made from glass is provided and a metal film 16 is deposited thereon using vapor deposition. One preferably metal is nickel however other metals may be used (e.g., gold, etc.). The metal film 16 is then coated with a positive (+) photoresist layer 18. Referring to FIGS. 2B and 3B, after coating the metal film 16 with a photoresist layer 18, photolithographic patterning using a mask defines the desired position for the nanowires. Etching then removes the exposed metal film 16, and etches in a side-exposed trench 20 through the metal film 16 as seen in FIGS. 2B and 3B. The etching solution may vary depending on the metal used in the metal film 16. For instance, nitric oxide may be used for nickel-based films. The trench 20 is electrically conductive (e.g., metallic) and is used as the working electrode in a three-electrode cell for electrodeposition of PEDOT nanowires from aqueous EDOT 2.5 mM EDOT, 12.5 mM LiClO$_4$, and, for virus-PEDOT hybrid nanowires 12, 10 nM M13 bacteriophage as seen in FIGS. 2C, 2D, 2E, 3C, 3D, and 3E.

Cyclic voltametry is used to deposit PEDOT 21 (as seen in FIG. 3C) as well as virus-PEDOT 23 (as seen in FIG. 3D) into the trench 20 region. In this operation, a potentiometer (not shown) is coupled to the trench 20 and varies the voltage as a function of time to deposit PEDOT and/or virus-PEDOT from solution. Voltage may vary from +1.025 V to –0.4V verses a saturated calomel electrode (SCE) at a rate of 20 mV/second. In the case where nickel is used as the metal film 16, a primer coat of neat PEDOT from a solution containing EDOT (2.5 mM) is first deposited in two cycles to help nucleate formation of the virus-PEDOT nanowires 12. The width of the pure PEDOT primer in is estimated by be 20 nm. For other metals such as gold, there is no need for first depositing a primer coat as virus-PEDOT may be directly deposited onto the metal. With respect to nickel, after the primer PEDOT has been deposited, this is followed by an exchange of the deposition solution for one containing both EDOT (2.5 mM) and M13 phage (10 nM). Both of these solutions also contained 12.5 mM LiClO$_4$, which was used to re-suspend the phage precipitated during isolation. In the M13-containing EDOT solution, six additional polymerization scans were carried out during which M13 incorporation into the nanowire 12.

The resultant nanowires 12 had a rectangular cross-section with widths dictated by the duration of electrodeposition and heights fixed by the thickness of the metal film 16 evaporated during the first step of the process. Exemplary dimensions for the nanowires may include widths on the order of around 200 nm and heights on the order of 60 nm. Efficient removal of the photoresist by acetone treatment, followed by further etching of the remaining metal film 16 with nitric acid (0.8 M), generated an array of freestanding virus-PEDOT nanowires 12 for electrical resistance measurements as seen in FIGS. 2E and 3E.

The fabrication process can be carried out in a conventional chemistry laboratory, and does not require a clean room. Unlike previous examples of viruses linked covalently or non-covalently to surfaces, the PEDOT synthesis allows for direct encapsulation of viruses into the interiors of nanowires 12. Synthesis of PEDOT nanowires requires $LiClO_4$ dissolved in a monomeric, aqueous solution of EDOT, and the $ClO_4^-$ anions are closely associated with the PEDOT nanowires 12 during the oxidative electrodeposition. This strategy takes advantage of the overall highly negatively charged surface of the phage, a property exploited previously for the coating of phage with cationic polymers. Thus, the viruses competed with $ClO_4^-$ ions for electrostatic incorporation into the nanowires 12, and remained stable through multiple steps including drying, washing, and treatment with both acetone and nitric acid (0.8 M). Further, the concentration of phage virus in the nanowire 12 may be increased by increasing the concentration of phage virus in solution prior to incorporation into the nanowire 12. Increasing the concentration of phage virus in the nanowire 12 can improve the overall sensitivity of the device 10 by increasing the concentration of phage-displayed receptors that are available for recognition of analytes.

The electrodeposition of virus-PEDOT nanowires 12 cannot be initiated from a solution containing both EDOT and M13 phage. Instead, a pure PEDOT "primer" was first electrodeposited from a solution containing EDOT (2.5 mM) without the M13 viruses which can be seen in FIGS. 2C and 3C. This PEDOT primer was electropolymerized by twice scanning the potential of the nickel LPNE electrode from 400 mV to 1.025 V versus a saturated calomel electrode (SCE) at 20 mV s$^{-1}$. The width of this pure PEDOT primer is estimated to be 20 nm. Next, the deposition solution was exchanged for one containing both EDOT (2.5 mM) and M13 phage (10 nM). Both of these solutions also contained 12.5 mM $LiClO_4$, which was used to re-suspend the phage during isolation. In the M13-containing EDOT solution, six additional polymerization scans were carried out during which M13 incorporation into the nanowire 12 occurred.

Figure 5A:
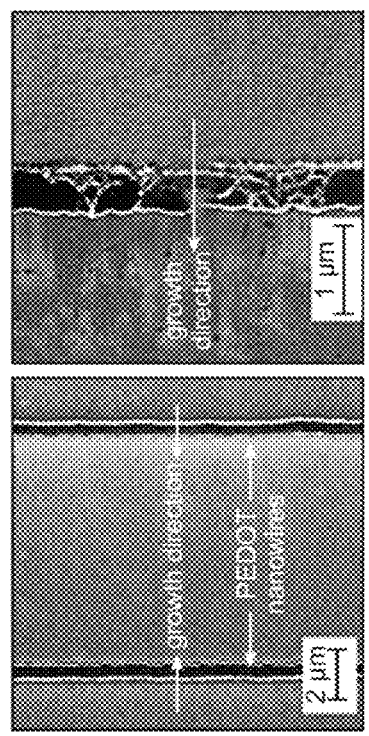
FIG. 5A is a Fourier Transform Infrared (FTIR) spectroscopy image of the PEDOT nanowire array.
Figure 5B:
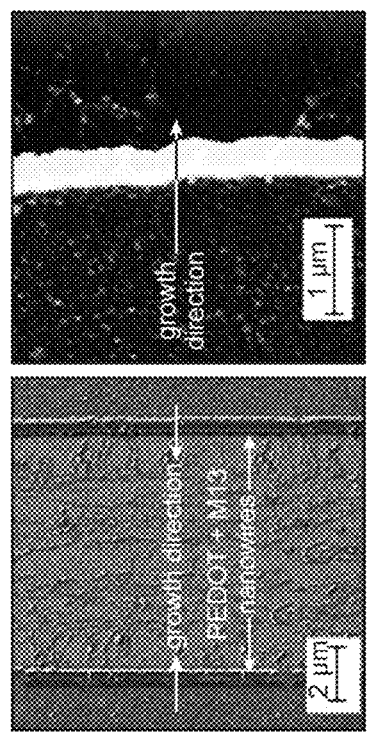
FIG. 5B is an inset view of FIG. 5A showing the indicated range of FTIR data from FIG. 5A.

The chemical composition of arrays of pure PEDOT nanowires 12 were characterized by FTIR and EDX. A comparison between a clean glass surface and an array of PEDOT nanowires supported on glass showed additional carbon content for the PEDOT nanowires as well as a significant sulfur signal, as expected for this compound. The transmission FTIR spectra of arrays of pure PEDOT nanowires produced seventeen (17) peaks assignable to PEDOT including strong stretches at 1515, and 1334 cm$^{-1}$ assigned to a C=C stretch and peaks at 1202, 1141, 1090, 1050 cm$^{-1}$ that are assigned to v(C—O—C) stretches. This can be seen in FIGS. 5A and 5B.

Figure 5C:
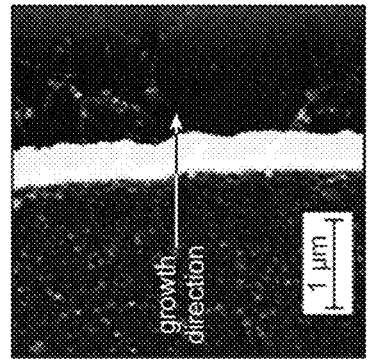
FIG. 5C is a secondary electron SEM image of PEDOT nanowires.
Figure 5D:
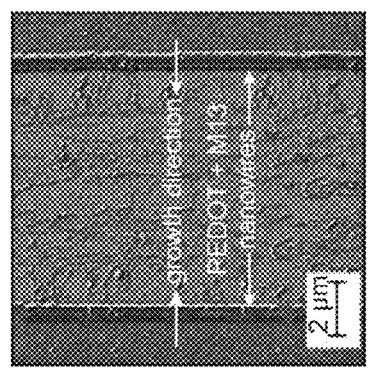
FIG. 5D is a secondary electron SEM image of virus-PEDOT wires, where M13 bacteriophage are observed as string-like particles within and between the nanowires.
Figure 5E:
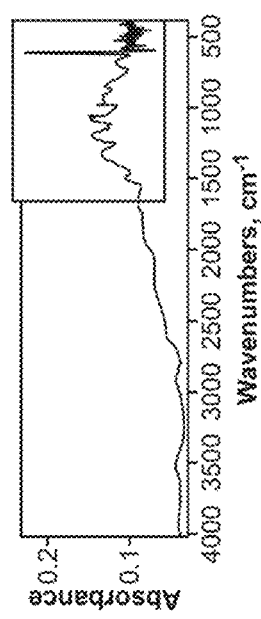
FIG. 5E is an in-lens secondary electron SEM image of a single virus-PEDOT wire, where viruses appear as conducting, fibrous particles within the nanowire.
Figure 5F:
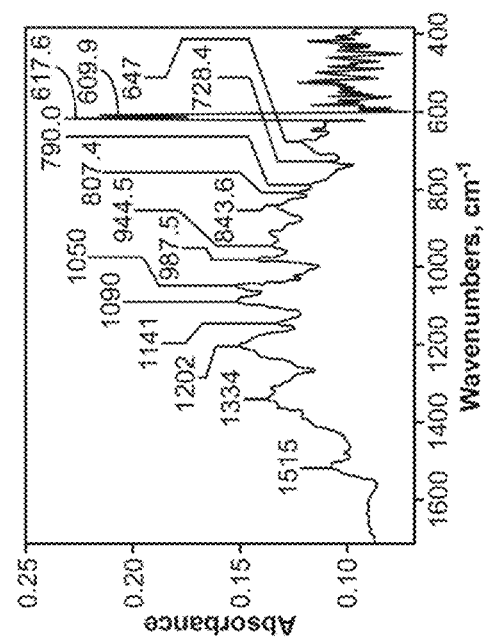
FIG. 5F is an atomic force microscope (AFM) image of a single virus-PEDOT wire.

FTIR spectra of virus-PEDOT nanowires 12 showed no additional spectral peaks assignable to the incorporated M13. Taken together, these data demonstrate that PEDOT nanowires can be prepared by LPNE. Several lines of evidence from SEM, AFM, fluorescence microscopy, and electrochemical biosensing support the incorporation of viruses into the conducting PEDOT nanowire arrays. First, clear differences between virus and non-virus PEDOT nanowires are evident in the SEM as seen, for example, in FIGS. 5C-5F and FIGS. 8A and 8B. Notably, the visualization of such viruses by this technique without sputter coating of a conductive material suggests the integration of the viruses into the conducting PEDOT nanowires. Fibrous structures with the dimensions of bundled filamentous viruses are clearly visible in FIGS. 5D-5F. The negative control nanowires synthesized in the absence of viruses do not have such particles (FIG. 5C). The small bundles of viruses can also be observed in AFM images, which appear quite distinct from the non-virus containing wires. FIG. 5F illustrates an AFM image illustrating the small bundles of viruses.

Figures 6A, 6B:
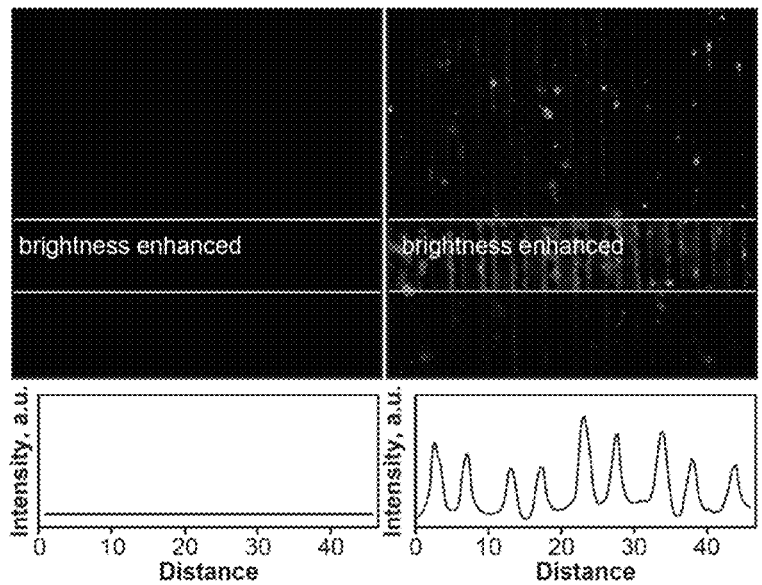
FIG. 6A is a fluorescence microscopy image of PEDOT nanowires after incubation with anti-M13 antibody conjugated to fluorescein. As expected, minimal fluorescence intensity is observed (lower panel).
FIG. 6B is a fluorescence microscopy image of virus-PEDOT nanowires following incubation with anti-M13 antibody conjugated to fluorescein shows localization of the viruses to the nanowires. Image J analysis quantifies the increased fluorescence intensity at the wires (lower panel).

Further characterization by fluorescence microscopy and biosensing both confirmed the successful incorporation of viruses into the PEDOT, and demonstrated that the viruses remained intact and fully functional for binding to analytes. A fluorescence assay applying an M13-specific antibody conjugated to fluorescein, followed by thorough wash steps, resulted in selective binding by the antibody to virus-functionalized nanowires results of which are presented in FIGS. 6A and 6B. This fluorescence proved the viruses were sufficiently exposed and functional to allow binding to the antibody. Furthermore, the viruses were very specifically incorporated, and highly localized to the virus-PEDOT nanowires, which can be clearly seen from the flat line trace (FIG. 6A) and the virus-PEDOT line trace (FIG. 6B) showing a pattern of periodic fluorescence corresponding to the patterning of the nanowires. In the absence of antibody, no fluorescence is observed.

Figure 7A:
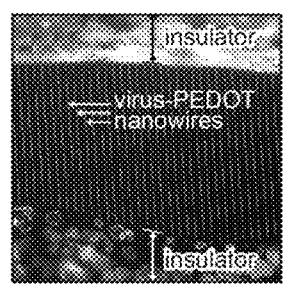
FIG. 7A is an optical micrograph of a virus-PEDOT nanowire array device.

Biosensing with the virus-PEDOT nanowire arrays further demonstrates successful incorporation of fully functional viruses. To fabricate biosensors based upon the nanowire arrays, silver wires 22 were coated with colloidal silver and pasted onto the nanowires exposing the virus-PEDOT nanowires for electrical biosensing measurements. Each device 10 included hundreds of parallel nanowires 12 have lengths of approximately 200-300 µm. The contacts were covered with an insulating paint 24 (e.g., lacquer) to prevent leaching into the liquid (FIG. 4C, 7A showing insulator). After thorough drying, the devices 10 were tested for resistance readings between 30 and 400 kΩ, which indicated a sufficient number of nanowires 12 in the array for reproducible biosensing. Using an applied bias (direct current), $E_{app}$=100 mV across the nanowire array, the current across, I, was measured and converted into resistance, $R=E_{app}/I$, which was recorded in real-time during immersion in phosphate buffered fluoride solution (PBF). Various applied DC currents will work beyond the 100 mV mentioned above. Following attainment of a stable baseline resistance, 15 µl aliquots containing known concentrations of the positive antibody (p-Ab), capable of binding to M13 viruses, or a negative control antibody (n-Ab), known not to bind the viruses, were pipetted onto the nanowires 12. FIG. 4A illustrates an resistance measurement device 26 (e.g., ohmmeter) connected to the silver contact wires 22 without exposure to either n-Ab or p-Ab. FIG. 4B illustrates that when n-Ab is applied to the device no material difference is resistance was detected as compared to the state of FIG. 4A. FIG. 4C illustrates the resistance measurement device 26 measuring increased resistance after p-Ab has been applied to the device 10. Upon observation of an increase in resistance and a saturated signal, the nanowires 12 were washed thoroughly with phosphate-buffered fluoride (PBF) (4.2 mM, $Na_2HPO_4$, 1.5 mM $KH_2PO_4$, and 140 mM NaF pH adjusted to 7.2 and sterile filtered through a 0.22 mm filter). The calibration plot shown in FIG. 7C shows the change in resistance from each injection of antibody, $\Delta R$, normalized by the initial electrical resistance measured in pure PBF buffer, $R_0$.

Figure 7B:
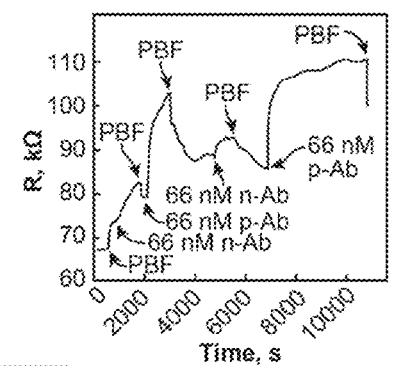
FIG. 7B is raw biosensing data, taken in real-time with the indicated injections of negative antibody (n-Ab), positive antibody (p-Ab), or washes with PBF buffer (PBF).
Figure 7C:
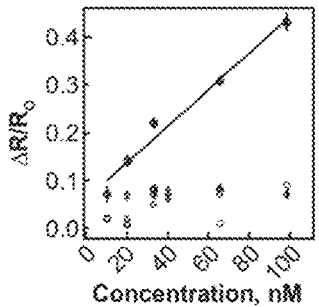
FIG. 7C is a compilation of real-time biosensing data, depicted as a calibration curve, in which the resistance change upon injection is plotted versus analyte concentration.
Figures 8A, 8B:
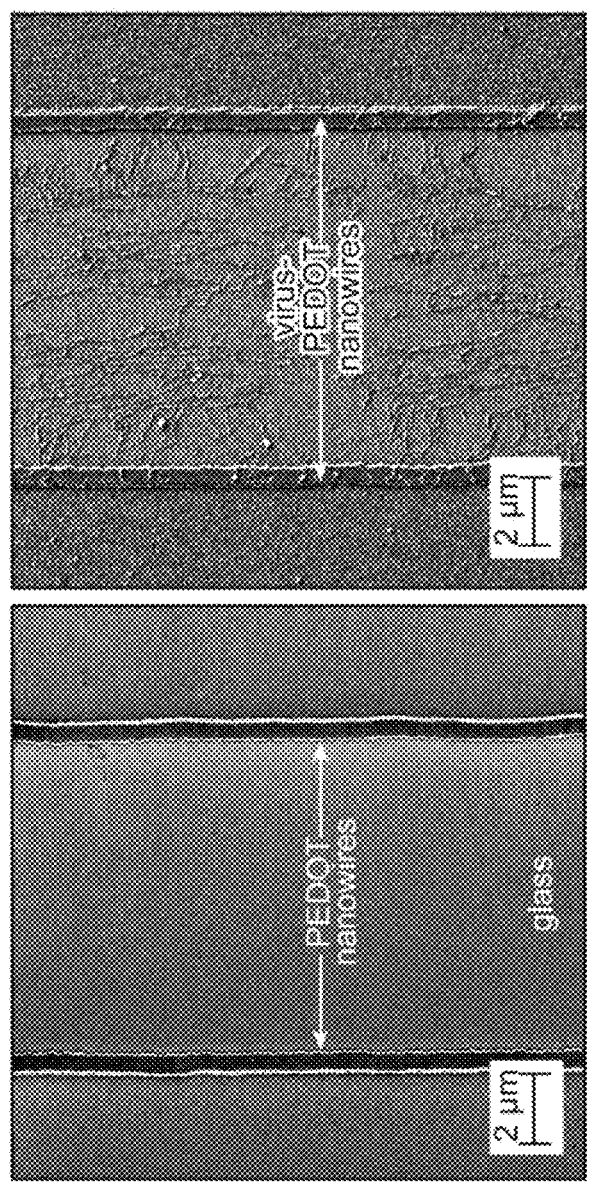
FIG. 8A is an electron micrograph of PEDOT nanowires (without viruses).
FIG. 8B is an electron micrograph of virus-PEDOT nanowires (with viruses). String-like particles are attached to the nanowires in FIG. 6B.

Analyte binding to the virus-PEDOT nanowires 12 resulted in a concentration dependent increase in resistance (upwardly sloping curve seen in FIG. 7C). At the highest concentrations of virus binding antibody (99 nM), an approximate 40% increase in the resistance ($\Delta R/R_0$) was observed. The lowest concentrations of analyte provide a limit of detection for this array of virus-PEDOT nanowires 12 in the range of 20 nM. Changes to phage-loading, device configuration, nanowire diameter and/or length could improve device sensitivity.

The mechanism of the resistance increase induced by p-Ab binding is incompletely understood, but one possibility is that the binding of p-Ab is induced by a charge-gating effect similar to that operating at semiconductor nanowires. Two negative controls support this hypothesis (FIG. 7C). First, treatment with PBF in the absence antibody shows no change in the resistance. Second, the negative antibody (anti-Flag antibody (n-Ab, Sigma), which again is known not to bind to the viruses, alters the resistance minimally, less than 10%. Furthermore, unmodified PEDOT nanowires, lacking the integrated viruses, changed resistance only minimally, less than 10%, upon treatment with both positive and negative antibody (FIG. 7C). Collectively, these data show that virus-PEDOT hybrid nanowires 12 are capable of directly electrically transducing the specific binding of an antibody to the entrained virus. The results thus demonstrate the viruses integrated into the PEDOT retain functionality, and can alter the properties of the nanowire through molecular recognition of analytes.

Real-time, reagent-free biosensing could provide an essential tool for early disease detection and diagnosis. Towards this goal, the reported virus-PEDOT nanowires provide an effective route for electrical resistance-based sensing in a buffer at physiologically relevant pH, ionicity, and room temperature. The viruses applied here, M13 bacteriophage, are readily amenable to tailoring of their surfaces for molecular recognition using phage display. Considering M13 as an exemplary filamentous phage, the phage virion consists of a stretched-out loop of single-stranded DNA (ssDNA) sheathed in a tube composed of several thousand copies of the major coat protein pVIII (product of gene VIII). Four minor coat proteins are found at the tips of the virion, each present in about 4-5 copies/virion: pIII (product of gene III), pIV (product of gene IV), pVII (product of gene VII), and pIX (product of gene IX). Of these, pIII and pVIII (either full length or partial length) represent the most typical fusion protein partners for polypeptides of interest. A wide range of polypeptides, including random combinatorial amino acid libraries, randomly fragmented chromosomal DNA, cDNA pools, antibody binding domains, receptor ligands, etc., may be expressed as fusion proteins e.g., with pIII or pVIII, for selection in phage display methods. In addition, methods for the display of multichain proteins (where one of the chains is expressed as a fusion protein) are also well known in the art. Thus, the generalizability of rgps such as M13 viruses to recognize a wide range of antigens and disease markers suggests the technique could find broad applicability to clinical diagnostics.

Eukaryotic viruses can also be used to display polypeptides on the biosensors described herein in an analogous manner to that described above using bacteriophage. For example, display of human heregulin fused to gp70 of Moloney murine leukemia virus has been reported by Han et al., Proc. Natl. Acad. Sci. USA 92: 9747-9751, 1995. Spores can also be used as replicable genetic packages. In this case, polypeptides are displayed from the outersurface of the spore. For example, spores from *B. subtilis* have been reported to be suitable. Sequences of coat proteins of these spores are provided by Donovan et al., J. Mol. Biol. 196: 1-10, 1987. Cells can also be used as replicable genetic packages. Polypeptides to be displayed are inserted into a gene encoding a cell protein that is expressed on the cells surface. Bacterial cells including *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli* are preferred. Details of outersurface proteins are discussed by U.S. Pat. No. 5,571,698, and Georgiou et al., Nat. Biotechnol. 15: 29-34, 1997 and references cited therein. For example, the lamB protein of *E. coli* is suitable.

Yeast display libraries have also been described. See e.g., Boder and Wittrup, Nat. Biotechnol. 15:553-7, 1997. Yeast surface expression systems can be used to express recombinant proteins on the surface of *S. cerevisiae* as a fusion with the a-agglutinin yeast adhesion receptor. Yeast expression can provide correct post-translational modification, processing and folding of mammalian proteins, coupled with rapid characterization of binding affinities of interacting proteins. The expressed fusion proteins can also contain c-myc and HA tag sequences, allowing quantification of the library surface expression by flow cytometry.

Polypeptides typically displayed from rgps fall into a number of broad categories. One category concerns short random or semi random peptides. For example, it is possible to produce libraries of short peptides in which some or all of the positions are systematically varied for the different amino acids. Random peptide coding sequences can be formed by the cloning and expression of randomly-generated mixtures of oligonucleotides is possible in the appropriate recombinant vectors. See e.g., Oliphant et al., Gene 44: 177-183, 1986.

A second category concerns variants of a starting framework protein. In this approach, a starting polypeptide is chosen and only selected positions are varied. The nucleic acid encoding the starting polypeptide can be mutagenized by, for example, insertion of mutagenic cassette(s) or error-prone PCR.

A third category consists of antibody libraries. Antibody libraries can be single or double chain. Single chain antibody libraries can comprise the heavy or light chain of an antibody alone or the variable domain thereof. However, more typically, the members of single-chain antibody libraries are formed from a fusion of heavy and light chain variable domains separated by a peptide spacer within a single contiguous protein. See e.g., Ladner et al., WO 88/06630; McCafferty et al., WO 92/01047. While expressed as a single protein, such single-chain antibody constructs can actually display on the surface of bacteriophage as double-chain or multi-chain proteins. See e.g., Griffiths et al., EMBO J. 12: 725-34, 1993. Alternatively, double-chain antibodies may be formed by noncovalent association of heavy and light chains or binding fragments thereof. The diversity of antibody libraries can arise from obtaining antibody-encoding sequences from a natural source, such as a nonclonal population of immunized or unimmunized B cells. Alternatively, or additionally, diversity can be introduced by artificial mutagenesis as discussed for other proteins.

The foregoing categories are exemplary in nature, and are not considered limiting. As one specific example of a biosensor, diagnostic makers (e.g., cancer markers or other molecular diagnostics) could be rapidly detected. Real-time, reagent-free detection of such diagnostic markers in biological fluids or other clinical samples could transform clinical diagnostics. As a potential solution, virus-based biosensors include both viruses for specific recognition of cancer markers and electrodes for transducing analyte detection. For virus electrode nanowire arrays, M13 bacteriophage are incorporated into an organic, electrically conducting polymer during electro-polymerization. Achieving real-time, specific detection of an M13-binding antibody via electrical resistance demonstrates device sensitivity for proteins comparable in size to numerous cancer markers. For prostate cancer marker detection, peptides binding to prostate-specific membrane antigen (PSMA) can be displayed on the phage surface. Affinity maturation by phage-displayed ligands can result in >1000-fold increase in binding affinity to PSMA. Incorporation of the improved PSMA-binding phage into the polymer nanowires would allow real-time, reagent-free detection of the prostate cancer marker, PSMA, in urine. Such simple and low-cost biosensors devices 10 would enables broad use for detection of numerous cancer and disease-related markers.

Figure 9:
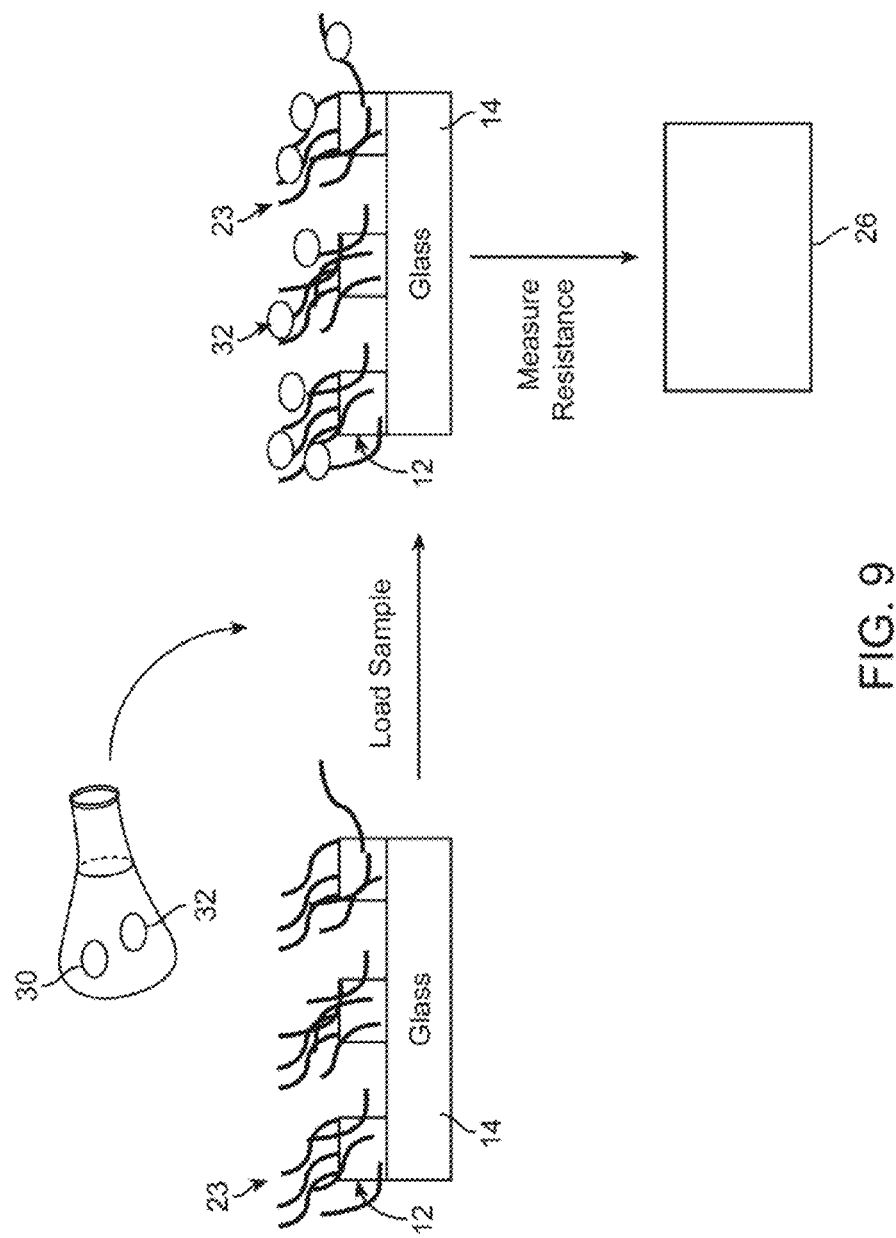
FIG. 9 illustrates a biosensor that comprises virus-PEDOT hybrid nanowires disposed on a glass substrate.

FIG. 9 illustrates one such biosensor device 10 that comprises virus-PEDOT hybrid nanowires 12 disposed on a glass substrate 14. As seen in FIG. 9, a sample 30 is added that contains a target analyte 32. The resistance is measured using resistance measurement device 26 such as an ohmmeter. By tracking changes in resistance, for example, by tracking current in response to an applied bias voltage, one can determine the presence or absence of a particular target analyte 32 that binds to the virus particles as illustrated in FIG. 7. A calibration curve can also be created like that illustrated in FIG. 7C such that concentrations could even be determined.

Figure 10:
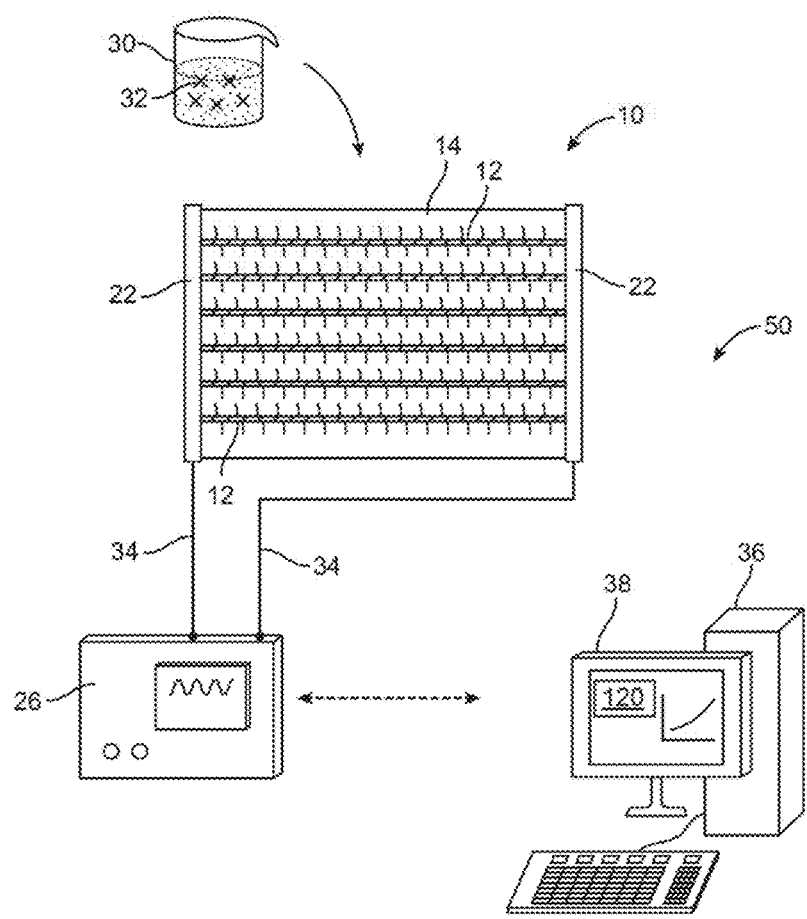
FIG. 10 illustrates a system and device according to one embodiment of the invention.

FIG. 10 illustrates a system 50 that includes a biosensor device 10. The biosensor device 10 includes an array of virus-PEDOT hybrid nanowires 12 disposed on a glass substrate 14. Silver wires 22 coated with colloidal silver make electrical contact with the nanowires 12. Electrical wires or other conductors 34 connect the silver wires 22 to a resistance measurement device 26 which may take the form of an ohmmeter or have ohmmeter functionality. The resistance measurement device 26 is also able to apply a biasing voltage ($E_{app}$) across the array of nanowires 12. The resistance measurement device 26 can then measure the current (I) across the nanowires 12. Resistance values (R) can be calculated using the following formula:

$$R = E_{app}/I \quad (1)$$

Resistance values can be determined in real time any may be displayed on the resistance measurement device 26 or transferred to, for example, a computer 36 that can then store, process, and display data to the end user. For example, the computer 36 may translate data obtained from the resistance measurement device 26 into a concentration of a target analyte 32. This translation may occur based for example, on calibration data that has previously been stored on the computer 36 that relates resistance measurements to concentration. This data may then be displayed to the user on a display 38 associated with the computer 36.

For example, in the system 50 of FIG. 10, in one example, the sample 30 may be a biological fluid such as urine and the target analyte 32 is PSMA—a known biomarker associated with prostate cancer. PSMA is a 750-residue, 100 kDa glycoprotein, which is overexpressed as a homodimer on the surface of prostate cancer cells; a differential mRNA splicing event leads to the expression of PSMA as an integral membrane protein specifically on prostate cancer cells. PSMA has been well characterized as a protein with diagnostic and prognostic capabilities for prostate cancer; for example, levels of PSMA correlate with the aggressiveness of tumor growth. Furthermore, elevated PSMA levels above nanomolar background concentrations are observed in the seminal fluid and urine of prostate cancer patients. The ready access to such samples makes PSMA an important target for the development of point-of-care and personal diagnostics.

The system 50 may be used to detect elevated levels of PSMA in the urine sample 30. This is done by contacting the sample 30 with the device 10 and monitoring the resistance values. If the monitoring resistance value translations into a concentration of PSMA that exceeds a pre-set threshold value, this indicates an elevated level of PSMA. This information may be used to then make clinical decisions regarding additional testing or therapeutic regimens (e.g., whether to perform a biopsy of the prostate). While PSMA and prostate cancer have been mentioned herein, this system 50 and the device 10 are able to monitor other antigens or biomarkers that bind with rgps. Rgps can be engineered to recognize essentially any analyte through binding to polypeptides on the viral surface. Libraries of phage-displayed proteins and peptides can be created for engineering recognition by manipulating the virus-packaged DNA. The phage display approach also provides an efficient method for improving the affinity of a known peptide sequence, termed affinity maturation. Following selections from a naïve library of phage-displayed peptides, the apparent affinities of the first generation selectants can be improved through additional phage-based mutagenesis and selections. One proven affinity maturation method applies a library composed of wild-type and homologous amino acid substitutions in every position of a starting peptide sequence, termed homolog shotgun scanning See e.g., Levin, A. M. et al., ACS Chem. Biol. 2007, 2, 493-500; and Murase, K. et al., Chem. Biol. 2003, 10, 161-168.

Experiment

High Affinity Virus-PEDOT Nanowires

A M13 phage homolog shotgun library was developed based upon a PSMA-binding ligand that was screened for higher affinity. Homolog shotgun scanning identified virus-displayed peptides with high sensitivity and specificity for the cancer-associated biomarker, PSMA. Then, the biomarker-specific viruses were encapsulated into an array of poly(3,4-ethylenedioxythiophene) (PEDOT) nanowires by lithographically patterned nanowire electrodeposition (LPNE). The resultant hybrid virus-nanowire arrays offer sensitive, real-time, reagent-free electrochemical biosensing of the cancer marker in both physiologically relevant buffer solutions and artificial urine.

Materials

All chemicals and reagents were purchased from Sigma-Aldrich and used as received unless otherwise noted. Anti-M13 antibody (p-Ab, GE Healthcare Life Sciences), KO7 helper phage, α-M13-HRP monoclonal antibody (Amersham Biosciences), and anti-FLAG-M2 antibody (n-Ab, Sigma) were used as received. PSMA was provided by Molecular Express, Inc. T4 Polynucleotide Kinase, T4 DNA Ligase, T7 DNA Polymerase, and all cell strains were obtained from New England Biolabs. All primers were synthesized by MWG Biotech. Milli-Q UV water was used as the solvent for all solutions. Phosphate-buffered fluoride (PBF, 4.2 mM $Na_2HPO_4$, 1.5 mM $KH_2PO_4$, and 140 mM NaF) was pH adjusted to 7.2 and sterile filtered through a 0.22 mm filter (Corning).

Synthesis of PSMA-2 Homolog Library

The DNA degeneracies used in the homolog scanning oligonucleotide are represented in the IUB code (K=G/T, M=A/C, R=A/G, S=G/C, W=A/T, Y=C/T, N=A/C/G/T, B=C/G/T, V=A/C/G). The oligonucleotide used is listed with mutations highlighted. Dsb-D6 HomScn: 5'-GCGTTTAGCGC-CAGCGCGTBGGASTGCGYCGA SGYCTWCMAV-MAVKSGTGCGASTKGGGTGGCGGCAGCG-GCAGCTCCAGCGGTGGA GGACCGGAGGAG-3' (SEQ ID NO:1). The homolog scanning libraries were constructed using an optimized oligonucleotide-directed mutagenesis protocol with the oligonucleotide Dsb-D6 HomScn and phagemid pJ1156 as template. Details regarding this construction may be found in Sidhu, S. S. et al., Methods Enzymol. 2000, 328, 333-363; and Kunkel, T. A. et al., Methods Enzymol. 1987, 154, 367-382 which are incorporated by reference herein.

Phagemid pJ1156 was identical to a previously described (Murase, K. et al., A. Chem. Biol. 2003, 10, 161-168) phagemid designed for phage display of proteins (pM1165a) with the following exception. The codons encoding the Stu II signal sequence upstream of the displayed protein were changed to a Dsb-A signal sequence to increase display levels.

PSMA-Binding Enzyme-Linked Immunosorbent Assay (ELISA)

A Nunc Maxisorp plate was coated with 10 µg/mL PSMA monomer or dimer protein for 1 h. The coating solution was removed, and the plate was blocked for 1 h with 0.2% BSA in PBS and washed 5 times with PT (300 µL/well). The wells were then incubated with phage displaying PSMA-binding peptides (100 µL/well) at the indicated concentrations for 1 h. After washing five times with PT, the plate was incubated with HRP-conjugated anti-M13 phage antibody (100 µL, 1:5000) in 0.1% PBT buffer for 30 min, and washed three times with PT, and twice with PBS. The plate was then developed using an o-phenylenediamine dihydrochloride/$H_2O_2$ solution (100 µL, 1 mg mL-1/0.02%) in citric acid buffer (50 mM citric acid, 50 mM $Na_2HPO_4$, pH 5.0), and the HRP activity was measured as absorbance at 450 nm.

Synthesis of Nanowires

PSMA-binding nanowire synthesis and PEDOT nanowire synthesis were conducted as described herein. Additional details may be found in Arter, J. A. et al., Nano Lett. 2010, 10, 4858-4862, which is incorporated by reference herein.

Device Construction and Measurements

After construction of the nanowire devices, Ag wires were pasted to the edges of the nanowires with colloidal Ag to form electrical contacts. Leads were connected from the device to a Keithley 2400 sourcemeter. An applied bias of 100 mV was applied across the nanowires and current was monitored as a function of time. This current can then be translated into a resistance per Equation 1 above.

Device fabrication applied lithographically patterned nanowire electrodeposition (LPNE) for the directed polymerization of EDOT mixed with phage. Control over the nanowire assembly allowed facile synthesis of several hundred, parallel virus-PEDOT nanowires on a glass substrate. This process first required vapor-based deposition of a nickel film on the glass substrate. After coating the nickel with a (+)-photoresist, photolithography exposed specific regions of the nickel for removal by treatment with nitric acid. The acid etching also undercuts the photoresist to produce a nickel-edged trench. Using the nickel edge as the working electrode in a three-electrode cell, virus-PEDOT nanowires were electropolymerized from aqueous 2.5 mM EDOT, 10 nM PSMA-binding viruses, and 12.5 mM $LiClO_4$; a primer coat of neat PEDOT, deposited by analogous protocols onto the nickel, helped nucleate formation of the virus-PEDOT nanowires. The remaining photoresist was removed by acetone treatment, followed by further etching of the exposed nickel with nitric acid (0.8 M). Each nanowire in the parallel array had a rectangular cross section, in which the duration of the electrodeposition and the thickness of the nickel layer dictated nanowire widths (≈200 nm) and heights (≈60 nm), respectively. As described below, the nanowires encapsulated PSMA-binding viruses, and retained electrical conductivity.

Biosensors applied the virus-PEDOT nanowires in a circuit for resistance measurements. To connect the virus-PEDOT nanowires to the sourcemeter, silver wires were coated with colloidal silver, and pasted onto the ends of nanowires. Next, the silver contacts were covered with an insulating lacquer to prevent the colloidal silver from leaching into the analyte solution. The exposed region of the virus-PEDOT nanowires included hundreds of parallel nanowires of ≈200 to 300 µm in length. The encapsulated viruses were visualized by scanning electron microscopy.

In addition to incorporation of the M13 viruses, electrodeposition provides site-specific control over the polymerization. Only the nickel trenches subjected to an oxidative potential become decorated with the virus-PEDOT nanowires, unlike less precise spotting techniques. During electrodeposition, perchlorate anions closely associate with the anodic, and thus positively charged, PEDOT nanowires. Here, a PSMA-binding peptide (amino acid sequence SECVEVFQNSCDW SEQ ID NO:2)) is displayed on the protein coat of the negatively charged M13 viruses, which are then incorporated into the PEDOT nanowires. The displayed peptide did not interfere with the association or encapsulation of the viruses into the PEDOT nanowires. Furthermore, the viruses and the PSMA-binding scaffolds remained stable and functional, despite the harsh treatments required for device assembly, including drying, washing, rinsing with acetone, and soaking in nitric acid as described above.

Affinity Maturation by Homolog Shotgun Scanning and Phage Display

The previously reported PSMA binding peptides, PSMA-1 (amino acid sequence, CALCEFLG (SEQ ID NO:3)) and PSMA-2 (amino acid sequence, LDCVEVFQNSCDW (SEQ ID NO:4)), were compared for affinity to the homodimeric and monomeric isoforms of PSMA. Details regarding PSMA-1 and PSMA-2 may be found in Yang, L. M. et al., Anal. Chem. 2006, 78, 3265-3270, which is incorporated by reference herein. Though diagnostically irrelevant, the monomeric isoform of PSMA provides a control for the binding specificity. As shown by phage-based ELISA, which can be seen in FIG. 11A, PSMA-2 binds with high affinity and specificity to the PSMA dimer, but not the monomer. PSMA-1 binds to both isoforms of PSMA. Chosen for its specificity to the PSMA dimer, the PSMA-2 sequence provided the template for an affinity maturation library targeting the PSMA dimer.

Figure 11:
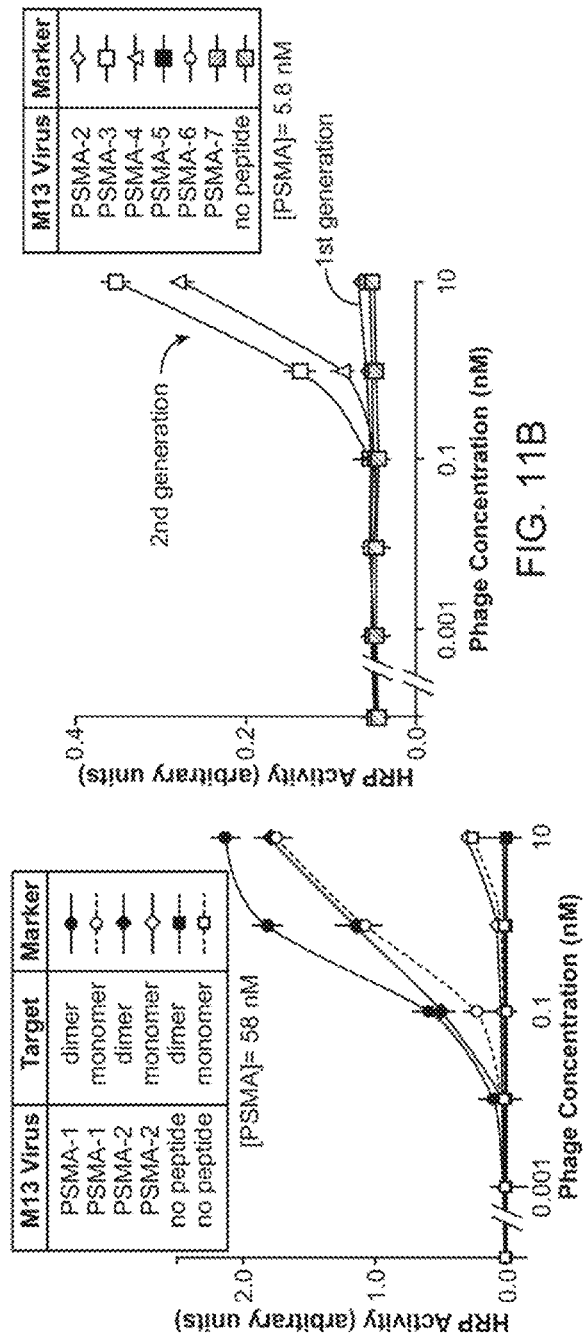
FIG. 11A illustrates phage-based ELISA results with the first generation PSMA-1 and PSMA-2 ligands with standard error (n=3).
FIG. 11B illustrates phage-based ELISA results with the affinity-matured, PSMA-binding selectants with standard error (n=3).
FIG. 11C illustrates the homolog-shotgun scanning library design used the PSMA-2 sequence as a template with programmed mutations bolded. PSMA-2 (amino acid sequence is LDCVEVFQNSCDW (SEQ ID NO:4).
FIG. 11D illustrates the homolog-shotgun scanning library design used the PSMA-2 sequence as a template with selected mutations bolded. PSMA-3: amino acid sequence SECVEVFQNSCDW (SEQ ID NO:2); PSMA-4: amino acid sequence SDCVEVFQNSCDW (SEQ ID NO:5); PSMA-5: amino acid sequence LECVEVYQNSCEW (SEQ ID NO:6); PSMA-6: amino acid sequence SECVEVFQNSCEL (SEQ ID NO:7); PSMA-7: amino acid sequence SDCVEVYQNSCDW (SEQ ID NO:8).
Figure 12:
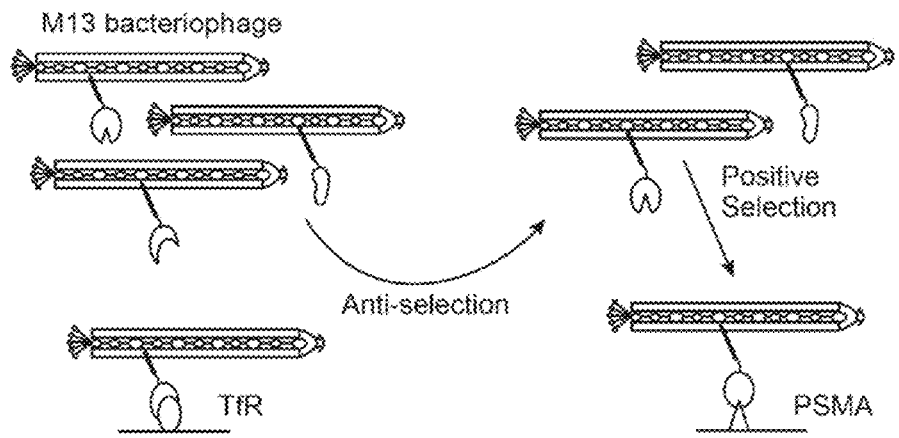
FIG. 12 illustrates a process of phage-based selections. Phage were selected against binding to the homologous transferrin receptor (TfR) in anti-selections. During positive selections, phage capable of binding to PSMA were isolated.

Homolog shotgun scanning of the PSMA-2 ligand applied combinatorial libraries of wild-type and closely related sidechains substituted for every amino acid of the peptide (FIG. 11C). The two Cys residues, expected to enforce conformational rigidity, remained invariant in the library. The experimental diversity of the Homolog library (≈2×10$^9$ different variants of PSMA-2) vastly exceeded the theoretical diversity for the library (1.84×10$^4$); thus, the library likely included all possible combinations of the wild-type and the homologous substitutions. Enrichment for five PSMA-binding peptide sequences emerged after three rounds of library selections. FIG. 12 illustrates phage-based selections. Anti-selections removed members of the library capable of binding to the transferrin receptor (TfR), which is a homolog of PSMA (54% identity), and the blocking agent bovine serum albumin (BSA).

Figure 13:
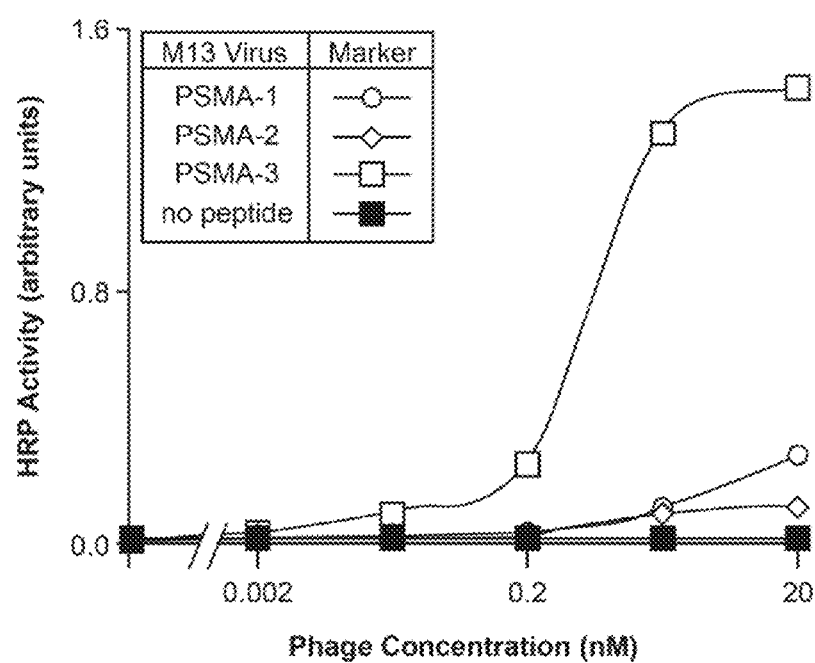
FIG. 13 illustrates phage-based ELISA ligands binding to PSMA homodimer (5.8 nM). The second generation peptide, PSMA-3, shows 1000-fold greater apparent affinity for the target versus the first generation, PSMA-2 ligand.

Next, the relative binding affinities of the five peptides selected from the homolog shotgun scanning library were compared. All selectants demonstrated equivalent or better affinity for the PSMA homodimer, than the parent peptide, PSMA-2. To provide a more sensitive test for evaluating binding affinity, the peptides were challenged to bind in half the time previously used for PSMA binding. Additionally, the target PSMA was coated on the microtiter plate with 10-fold lower concentration. This higher screening stringency can better distinguish high from moderate affinity binders. The more stringent ELISA results as seen in FIGS. 11B and 13 demonstrates that peptides PSMA-3 and PSMA-4 possess a 100- to 1000-fold higher affinity towards PSMA, than the starting template, PSMA-2. As expected, the negative control phage, which lack a displayed peptide, fail to bind PSMA.

Analysis of the peptide sequences and their relative binding affinities could uncover structure-activity relationships required for high affinity binding to PSMA. The 11 C-terminal residues of PSMA-3 were largely conserved for all selectants from the homolog library (FIG. 11D). Thus, this core sequence appears critical for the molecular recognition of PSMA. Two substitutions incorporated into the sequence of PSMA-3 (L1S and D2E) dramatically enhanced the apparent binding affinity for PSMA. The Ser substitution provides a more polar sidechain, which can potentially donate a hydrogen bond, improving the surface complementarity to PSMA. The selection of Glu in place of Asp extends the sidechain length by one methylene; this substitution maintains the contribution to binding by the carboxylate functionality, and the length extension could allow for new interactions. Increased avidity could also enhance the apparent binding affinity of the PSMA-3 ligand for PSMA, if the PSMA-3 peptide expresses more robustly on the phage surface than the PSMA-2 sequence. PSMA-3 shows specific binding for the PSMA dimer, but not PSMA monomer, TfR, casein, or various other proteins. In summary, PSMA-3 offers substantially higher binding affinity than PSMA-2 to the PSMA homodimer, and such improved binding can provide sensitive detection of PSMA in nanodevices.

Real-Time Biosensing with PSMA-Binding Nanowires in Buffer and Synthetic Urine

Following encapsulation of PSMA-3 viruses into PEDOT and nanowire device construction, biosensing measurements monitored changes in the electrical resistance across the virus-PEDOT nanowires. Using an applied bias, $E_{app}=100$ mV across the nanowire array, the current, I, was measured, and converted into resistance using Equation 1 above. The measurements were recorded in real-time during immersion in phosphate-buffered fluoride solution with various analytes. The analyte was pipetted directly onto the nanowire array (15 ml aliquots), and real-time changes in electrical resistance were observed. After each analyte injection, the wires were washed thoroughly with buffer.

Figure 14A:
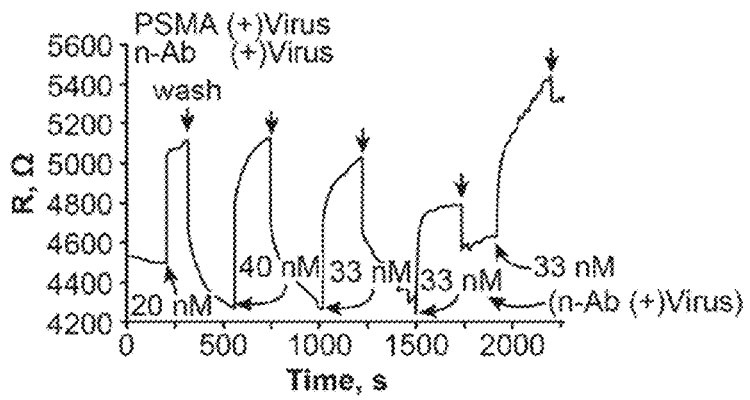
FIG. 14A illustrates a real-time trace of biosensing data of resistance as a function of time with the indicated injections of negative antibody (n-Ab), PSMA, or washes with PBF buffer (black arrows). PSMA was injected periodically with the exception of a single injection of n-Ab at around 1500 seconds.
Figure 14B:
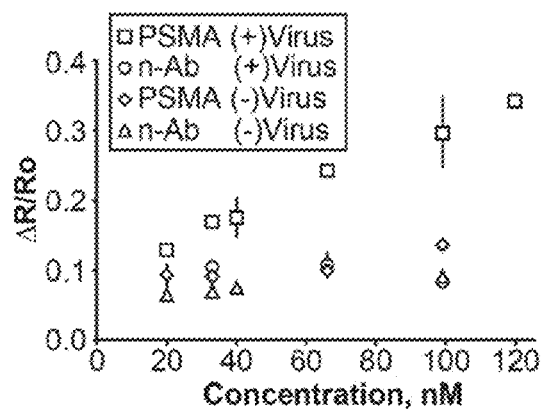
FIG. 14B illustrates a compilation of all real-time biosensing data, depicted as a calibration curve using standard deviation (n=3). The change in resistance $\Delta R/R_o$ upon injection is plotted versus analyte concentration (nM).

In monitoring the change in resistance of the virus-PEDOT wires, nanowires with PSMA-3 viruses encapsulated showed a sensitive and specific increase in resistance upon addition of the prostate cancer marker PSMA as seen in FIG. 14A. The binding of PSMA to the nanowires results in a concentration dependent increase in the electrical resistance. A calibration plot for PSMA sensing by tailored virus-PEDOT nanowires demonstrates a linear correlation between the normalized change in resistance ($\Delta R/R_o$) and the concentration of the added PSMA (FIG. 14B), where $R_o$ is the initial electrical resistance measured in pure buffer. The negative control antibody, which is known not to bind to the phage, resulted in little change in the resistance. A high concentration of PSMA (120 nM) yields a 35% change in resistance of the wires. The lowest concentrations provide a limit of detection in the range of 25 nM. Changes to the concentrations of encapsulated phage and displayed peptide, the device configuration and the nanowire dimensions could improve device sensitivity.

Though incompletely understood, three possible mechanisms could account for the increased resistance of the virus-PEDOT nanowires in response to PSMA binding. First, the binding could displace the ionically conductive buffer solution from the nanowires. A related second mechanism could involve PSMA molecules blocking the transport of ions through the nanowires. Both mechanisms increase the ionic resistance of the nanowires by decreasing the accessibility of ions. Third, binding to the PSMA-3 virus-nanowires could induce a charge-gating effect similar to observations with semiconductor nanowires. This concept is supported by negative controls with both buffer alone and non-binding antibody, which both show minimal changes in resistance at the virus-nanowires. These data indicate that modified viruses, upon incorporation into PEDOT nanowires, are capable of directly electrically transducing the specific binding of a cancer marker to the PSMA-3 peptide. The virus-PEDOT nanowires can be readily tailored by changing the displayed peptide on the surface of the virus, which can alter the molecular recognition for detection of other analytes in solution.

Figure 14C:
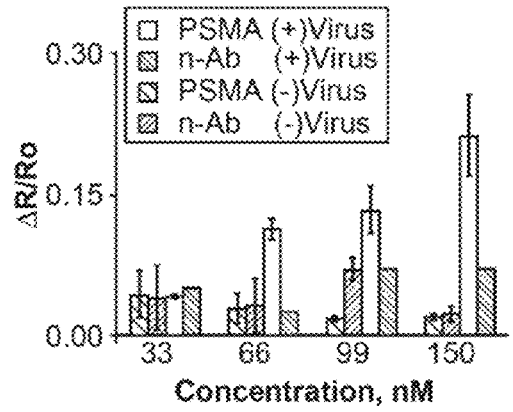
FIG. 14C is a bar graph of change in resistance upon injection of PSMA (+) virus, n-Ab (+) virus, PSMA (–) virus, and n-Ab (–) virus in a solution of synthetic urine at different concentration. A standard deviation (n=3) was used.

The robustness of virus-PEDOT nanowire biosensors and their potential applicability to clinical diagnostics were explored for the detection of PSMA added to artificial urine. Such measurements can be challenging, as urine includes a large number of components (18 in artificial urine), high salt and a pH of 5.8.31 PSMA was doped into the solution, and used for biosensing with PSMA-3-PEDOT, and PEDOT nanowires as a control. Wires bearing the PSMA-binding recognition motif showed specific binding to PSMA in urine as seen in FIG. 14C.

All publications mentioned here are specifically incorporated by reference. While embodiments of the present invention have been shown and described, various modifications may be made without departing from the scope of the present invention. The invention, therefore, should not be limited, except to the following claims, and their equivalents.

What is claimed is:

1. A method of making a device comprising:
   depositing a metallic film on a substrate;
   coating the metallic film with a photoresist;
   patterning the photoresist to define desired portions of electrodes;
   removing portions of the exposed metallic film to form the electrodes;
   electrodepositing bacteriophage-PEDOT on the electrodes by cyclical electrodeposition of a solution containing 3,4-ethylene dioxythiophene (EDOT), LiClO$_4$, and bacteriophage; and
   securing electrical contacts to the bacteriophage-PEDOT electrodes.

2. The method of claim 1, wherein the metallic film comprises nickel, and wherein electrodepositing bacteriophage-PEDOT electrodes comprises a first electrodeposition of a PEDOT primer from a solution of 3,4-ethylene dioxythiophene (EDOT) and LiClO$_4$ followed by a subsequent electrodeposition of 3,4-ethylene dioxythiophene (EDOT), LiClO$_4$, and bacteriophage.

3. The method of claim 1, wherein the bacteriophage displays a proteinaceous heterologous molecule on its surface.

4. The method of claim 3, wherein said proteinaceous heterologous molecule is selected from the group consisting of peptides, nucleic acids, antibody binding domains, and receptor ligands.

5. The method of claim 1, wherein the bacteriophage comprises M13 bacteriophage.

6. The method of claim 1, wherein the bacteriophage contained in the bacteriophage-PEDOT electrodes comprises moieties configured to bind to prostate-specific membrane antigen (PSMA).

7. A biosensor comprising:
   a substrate;
   at least one bacteriophage-PEDOT electrode disposed atop the surface of the substrate; and
   a resistance measuring device operatively coupled to the at least one bacteriophage-PEDOT electrode.

8. The biosensor of claim 7, wherein the bacteriophage displays a proteinaceous heterologous molecule on its surface.

9. The method of claim 8, wherein said heterologous molecule is selected from the group consisting of peptides, antibody binding domains, and receptor ligands.

10. The biosensor of claim 8, wherein the bacteriophage comprises M13.

11. The biosensor of claim 8, wherein the bacteriophage is selected from the group consisting of lambda phage, T-even phage, and T-odd phage.

12. The biosensor of claim 7, further comprising a computer operatively connected to the resistance measuring device.

13. The biosensor of claim 7, wherein the bacteriophage-PEDOT electrode comprises moieties configured to bind to prostate-specific membrane antigen (PSMA).

14. The biosensor of claim 13, wherein the moieties comprise a peptide.

15. The biosensor of claim 14, wherein the peptide comprises PSMA-3.

16. The biosensor of claim 7, wherein the at least one bacteriophage-PEDOT electrode binds to PSMA.

17. A method of using the biosensor of claim 7, further comprising applying a sample to the biosensor and monitoring the resistance of the at least one bacteriophage-PEDOT electrode and detecting a target based on the monitored resistance.

18. The method of claim 17, wherein an increase in monitored resistance corresponds to the presence of the target analyte.

19. A method of making a device comprising:
- forming at least one electrode on a substrate;
- securing electrical contacts to the at least one electrode;
- exposing the at least one electrode to a solution containing 3,4-ethylene dioxythiophene (EDOT), $LiClO_4$, and virus bacteriophage; and
- applying a cyclic voltage to the at least one electrode via the electrical contacts so as to electrodeposit virus bacteriophage-PEDOT on the at least one electrode.

* * * * *

SEQUENCE LISTING

<160> NUMBER OF SEQ ID NOS: 4

<210> SEQ ID NO 1
<211> LENGTH: 99
<212> TYPE: DNA
<213> ORGANISM: Artificial Sequence
<220> FEATURE:
<223> OTHER INFORMATION: Synthetic oligonucleotide

<400> SEQUENCE: 1
gcgtttagcg ccagcgcgtb ggastgcgyc gasgyctwcm avmavksgtg cgastkgggt    60

```
ggcggcagcg gcagctccag cggtggagga ccggaggag                        99
```

```
<210> SEQ ID NO 2
<211> LENGTH: 13
<212> TYPE: PRT
<213> ORGANISM: Artificial Sequence
<220> FEATURE:
<223> OTHER INFORMATION: Synthetic oligopeptide

<400> SEQUENCE: 2

Ser Glu Cys Val Glu Val Phe Gln Asn Ser Cys Asp Trp
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Synthetic oligopeptide

<400> SEQUENCE: 3

Cys Ala Leu Cys Glu Phe Leu Gly
1               5

<210> SEQ ID NO 4
<211> LENGTH: 13
<212> TYPE: PRT
<213> ORGANISM: Artificial Sequence
<220> FEATURE:
<223> OTHER INFORMATION: Synthetic oligopeptide

<400> SEQUENCE: 4

Leu Asp Cys Val Glu Val Phe Gln Asn Ser Cys Asp Trp
1               5                   10
```